United States Patent
Van Den Bergen et al.

(10) Patent No.: US 10,941,271 B2
(45) Date of Patent: Mar. 9, 2021

(54) (METH)ACRYLATED COMPOUNDS BASED ON RECYCLED PET

(71) Applicant: ALLNEX Belgium S.A., Drogenbos (BE)

(72) Inventors: Hugues Van Den Bergen, Drogenbos (BE); Paul Gevaert, Geraardsbergen (BE); Stephan Peeters, Heverlee (BE)

(73) Assignee: ALLNEX BELGIUM S.A., Drogenbos (BE)

( * ) Notice: Subject to any disclaimer, the term of this patent is extended or adjusted under 35 U.S.C. 154(b) by 148 days.

(21) Appl. No.: 16/314,759

(22) PCT Filed: Jul. 10, 2017

(86) PCT No.: PCT/EP2017/067186
§ 371 (c)(1),
(2) Date: Jan. 2, 2019

(87) PCT Pub. No.: WO2018/011098
PCT Pub. Date: Jan. 18, 2018

(65) Prior Publication Data
US 2019/0153191 A1    May 23, 2019

(30) Foreign Application Priority Data

Jul. 12, 2016 (EP) .................................... 16179074

(51) Int. Cl.
| | | |
|---|---|---|
| *C08G 63/91* | (2006.01) | |
| *C08J 11/24* | (2006.01) | |
| *C09D 11/104* | (2014.01) | |
| *C08G 63/48* | (2006.01) | |
| *C09J 167/07* | (2006.01) | |
| *C09D 167/07* | (2006.01) | |
| *C08G 63/183* | (2006.01) | |
| *C08G 63/47* | (2006.01) | |
| *C09D 11/101* | (2014.01) | |
| *C07C 67/02* | (2006.01) | |
| *C07C 67/03* | (2006.01) | |

(52) U.S. Cl.
CPC .............. *C08J 11/24* (2013.01); *C07C 67/02* (2013.01); *C07C 67/03* (2013.01); *C08G 63/183* (2013.01); *C08G 63/47* (2013.01); *C08G 63/48* (2013.01); *C08G 63/91* (2013.01); *C09D 11/101* (2013.01); *C09D 11/104* (2013.01); *C09D 167/07* (2013.01); *C09J 167/07* (2013.01); *C08J 2367/02* (2013.01)

(58) Field of Classification Search
CPC ....... C08J 11/24; C08J 2367/02; C08G 63/48; C08G 63/183; C08G 63/47; C08G 63/91; C08G 63/914; C08G 63/916; C09J 167/07; C09D 167/07; C09D 11/101; C09D 11/104; C07C 67/02; C07C 67/03
See application file for complete search history.

(56) References Cited

U.S. PATENT DOCUMENTS

| | | | | | |
|---|---|---|---|---|---|
| 6,127,436 | A | * | 10/2000 | Chatterjee | ............... C08G 63/20 521/48.5 |
| 6,686,399 | B1 | * | 2/2004 | Kawamura | ............ C08G 63/48 521/48 |

(Continued)

FOREIGN PATENT DOCUMENTS

| | | |
|---|---|---|
| EP | 1 178 092 | 2/2002 |
| EP | 2 325 229 | 5/2011 |

(Continued)

OTHER PUBLICATIONS

International Search Report dated Aug. 14, 2017 in International Application No. PCT/EP2017/067186.

(Continued)

*Primary Examiner* — Robert C Boyle
(74) *Attorney, Agent, or Firm* — Wenderoth, Lind & Ponack, L.L.P.

(57) ABSTRACT

The present invention relates to a process for preparing a polyester (meth)acrylate resin (I), said process comprising the steps of: (a) Reacting a thermoplastic polyester with (a1) at least one polyhydric alcohol and, optionally, with (a2) at least one triglyceride, wherein the molar ratio of triglyceride to thermoplastic polyester is between 0 and 0.3, and the molar ratio of polyhydric alcohol to thermoplastic polyester is at most 1.9 to obtain a depolymerization product A that has a hydroxyl number within the range of from 200 to 800 mg KOH/g; (b) Reacting the depolymerization product A with (b1) at least one fatty acid and/or (b2) at least one polybasic carboxylic acid and, optionally, with (b3) at least one polyhydric alcohol to provide a polyester polyol B; (c) Reacting the polyester polyol B with (c) at least one (meth) acrylating compound to provide a (meth)acrylated compound (I), wherein the weight ratio of fatty acid (b 1) to the depolymerization product A is between 0 and 0.6, wherein the weight ratio of polybasic carboxylic acid (b2) to the depolymerization product A is less than 0.3, wherein the weight ratio of (meth)acrylating compounds (c) to the depolymerization product A is between 0.1 and 0.8, and wherein the (meth)acrylated compound (I) that is obtained has a number average molecular weight (Mn) of between 500 and 5,000 Dalton. Typically PET is used as starting material. Typically compounds (I) of the invention have a PET content of at least 15 wt %, preferably at least 25 wt %. The present invention also relates to (meth)acrylated compounds (I) thus obtained and to coating compositions and inks based upon these materials. Materials of the invention allow the use of a high amount of PET waste. Inks and coatings prepared from these materials exhibit an excellent pigment wetting and/or ink-water balance.

17 Claims, No Drawings

(56) References Cited

U.S. PATENT DOCUMENTS

| | | | |
|---|---|---|---|
| 2002/0042486 A1* | 4/2002 | Moya | C09J 167/07 |
| | | | 526/320 |
| 2012/0220676 A1* | 8/2012 | Moens | C08G 63/916 |
| | | | 521/48.5 |
| 2015/0344622 A1* | 12/2015 | Mukerjee | C08G 63/553 |
| | | | 521/172 |
| 2016/0053058 A1 | 2/2016 | Tabor et al. | |
| 2017/0022318 A1 | 1/2017 | Gaudl et al. | |

FOREIGN PATENT DOCUMENTS

| | | |
|---|---|---|
| JP | 2003-26741 | 1/2003 |
| WO | 2015/164331 | 10/2015 |
| WO | 2015/171432 | 11/2015 |
| WO | 2015/171433 | 11/2015 |

OTHER PUBLICATIONS

Written Opinion of the International Searching Authority dated Aug. 14, 2017 in International Application No. PCT/EP2017/067186.

\* cited by examiner

(METH)ACRYLATED COMPOUNDS BASED ON RECYCLED PET

The present invention relates to (meth)acrylated compounds which are prepared by depolymerizing a thermoplastic polyester, followed by a condensation and a (meth) acrylation reaction. Often a virgin, scrap, recycled or reclaimed PET is used as starting material. The process of the invention allows the incorporation of high amounts of recyclable materials. Inks and coatings prepared from e.g. polyester (meth)acrylates and urethane (meth)acrylates of the invention have an improved pigment wetting and ink-water balance. Also flow and gloss are often improved.

Some thermoplastic polyesters and more in particular polyalkylene terephthalates can be recycled, at least in part. Poly(ethylene terephthalate), commonly known as PET, is used extensively in the manufacture of fibers, photographic films and soft drinks bottles. PET production offers a tremendous convenience in our lives and daily life would be quite different without it. However, the amount of PET waste is increasing drastically and a recycling process must be established for the preservation of resources and the protection of the global environment. Recycling of waste PET, either post-consumer or non-post-consumer, is a worldwide concern due to its environmental impact and the increasing volume of these materials being produced by society. Glycolysis of PET is one of the most widely studied processes for PET depolymerization.

Energy curable coating compositions and inks have become increasingly popular because they do not employ volatile organic solvents and thus avoid the associated health and environmental concerns. They are applicable in a wide range of printing techniques and cure rapidly upon irradiation. Curing of energy curable coating compositions and inks predominantly proceeds via a radical polymerization mechanism. Radiation curable compositions and UV curable compositions in particular are most popular.

WO 2015/164331 (Sun) relates to a method for preparing polyester acrylates having a number average molecular weight of at least 800 Da from recycled polyethylene terephthalate (PET).

WO 2015/171433 and WO 2015/171432 (Resinate Materials) describe polyester polyols and polyester acrylates prepared from PET using glycols and dimer fatty acids, wherein the molar ratio of dimer fatty acids to thermoplastic polyester is less than 0.8, the molar ratio of glycol to thermoplastic polyester is at least 2.0, and the polyester polyols have a hydroxyl number within the range of from 25 to 800 mg KOH/g. In these references the glycol/thermoplastic polyester molar ratio is at least 2, and therefore the recycled PET content is fairly low.

It is an object of the invention to provide a way to produce (meth)acrylated compounds with a higher recycled content. At the same time the (meth)acrylates formed should be easy to incorporate into coating compositions and inks and should have an excellent pigment wetting and/or ink-water balance.

Against this background of the invention we now provide a process for preparing (meth)acrylated compounds (I), said process comprising the steps of:
(a) Reacting a thermoplastic polyester with (a1) at least one polyhydric alcohol and, optionally, with (a2) at least one triglyceride, wherein the molar ratio of triglyceride to thermoplastic polyester is between 0 and 0.3, and the molar ratio of polyhydric alcohol to thermoplastic polyester is at most 1.9 to obtain a depolymerization product A with a hydroxyl number within the range of from 200 to 800 mg KOH/g;
(b) Reacting the depolymerization product A with (b1) at least one fatty acid and/or (b2) at least one polybasic carboxylic acid different from (b1) and, optionally, with (b3) at least one polyhydric alcohol to provide a polyester polyol B;
(c) Reacting the polyester polyol B with at least one (meth)acrylating compound (c) to provide a methacrylated compound (I),
wherein the weight ratio of fatty acid to the depolymerization product A is between 0 and 0.6, wherein the weight ratio of polybasic carboxylic acid to the depolymerization product A is less than 0.3, wherein the weight ratio of (meth)acrylating compounds to the depolymerization product A is between 0.1 and 0.8, and wherein the (meth)acrylated compound (I) has a number average molecular weight (Mn) between 500 and 5,000 Da,
with the proviso that at least one triglyceride (a2) and/or at least one fatty acid (b1) is used to prepare the (meth)acrylated compounds (I) of the invention.

Advantageously the (meth)acrylated compound (I) of the invention has at least one triglyceride (a2) and/or at least one fatty acid (b1) incorporated into its structure. In an embodiment of the invention, at least one triglyceride is incorporated and advantageously no fatty acid. In another embodiment of the invention at least one fatty acid is incorporated and advantageously no triglyceride. In yet another embodiment at least one triglyceride and at least one fatty acid are incorporated into the structure of the (meth)acrylated compound (I) of the invention. The term fatty acid covers mono fatty acids as well as polymerized fatty acids such as dimer fatty acids and/or trimer fatty acids. In the context of the invention the fatty acid typically is a polymerized fatty acid and most typically it is a dimer fatty acid and/or a trimer fatty acid. Dimer fatty acids are preferred.

In the context of the present invention the term "(meth)acrylate" is meant to designate that the compound has one or more acryloyl groups and/or one or more methacryloyl groups.

The thermoplastic polyester is typically selected from one or more of the group consisting of: polyethylene naphtalate (PEN); polyethylene terephthalate (PET); polypropylene terephthalate (PPT); polybutylene terephthalate (PBT); polytrimethylene terephthalate; glycol-modified polyethylene terephtalate; copolymers of terephthalic acid and 1,4-cyclohexanedimethanol; isophthalic acid-modified copolymers of terephthalic acid and 1,4-cyclohexanedimethanol; polyhydroxy alkanoates; copolymers of diols with 2,5-furandicarboxylic acid or dialkyl 2,5-furandicarboxylates; copolymers of 2,2,4,4-tetramethyl-1,3-cyclobutanediol with isophthalic acid, terephthalic acid or orthophthalic derivatives; dihydroferulic acid polymers. Polyalkylene terephthalates are generally preferred. By a "polyalkylene terephthalate" is meant in particular polybutylene terephthalate (PBT), polypropylene terephthalate (PPT) and/or polyethylene terephthalate (PET). Preferred in the context of the invention is polyethylene terephthalate (PET).

In general the (meth)acrylated compounds (I) of the invention have a polyalkylene terephthalate (in casu PET) content of at least 15 wt %, preferably at least 20 wt %, and most preferably at least 25 wt % (based on the total weight of the (meth)acrylated compound (I)).

The first step of the process of the invention—step (a)—comprises the step of depolymerizing the thermoplastic polyester (in particular PET) via an alcoholysis reaction with one or more polyhydric alcohols. Often the "reacting" in step (a) comprises (or consists of) heating the thermoplastic polyester, in casu PET, in the presence of one or more glycols to give a polyester polyol intermediate A (the "depolymerization product").

In this first step (a), a depolymerization product A is formed that has a hydroxyl number within the range of from 200 to 800 mg KOH/g. Usually the hydroxyl number is at least 225 mg KOH/g, typically at least 250 mg KOH/g. Usually the hydroxyl number is at most 700 mg KOH/g, typically at most 600 mg KOH/g. The hydroxyl number is measured by titration of acetic acid after acetylation of hydroxyl groups and hydrolysis of acetic anhydride excess. The method for measuring the hydroxyl number is fully described in the examples. Advantageously, the molar ratio of triglyceride to thermoplastic polyester (in casu PET) is between 0 and 0.3. Typically this ratio is between 0 and 0.25, more in particular between 0 and 0.2. If a triglyceride is being used for the preparation of the (meth)acrylated compound (I) of the invention then this ratio typically is between 0.01 and 0.3, more in particular between 0.01 and 0.25 and most in particular between 0.05 and 0.2. Advantageously, the molar ratio of polyhydric alcohol to thermoplastic polyester (in casu PET) is lower than 2. Typically this ratio is at most 1.9, more typically at most 1.8. Preferably this ratio is lower than 1.9, more preferably it is lower than 1.8, typically it is lower than 1.7, and in some embodiments it can be lower than 1.6.

Catalysts suitable for making the digested intermediate (the "depolymerization product") in step (a) are well known (see, e.g., K. Troev et al., J. A I. Pol m. Sci. 90 (2003) 1148). Suitable catalysts include e.g. titanium, zinc, antimony, germanium, zirconium, manganese, or other metals. Specific examples include titanium alkoxides (e.g. tetrabutyl titanate), titanium(IV) phosphate, zirconium alkoxides, zinc acetate, lead acetate, cobalt acetate, manganese(II) acetate, antimony trioxide, germanium oxide etc, and mixtures thereof. Catalysts that do not significantly promote isocyanate reaction chemistries are preferred. The amount of catalyst used is typically in the range of from 0.005 to 5 wt % (weight percent), preferably from 0.01 to 1 wt %, more preferably from 0.02 to 0.7 wt %, relative to the total amount of polyol (also referred to the depolymerization product") being prepared in step (a).

The PET preferentially used as starting material in the process of the invention may be derived from polymerizing terephthalic acid and ethylene glycol (virgin PET), but is preferably derived from waste material generated in the PET production process and waste materials generated in the production of PET molded articles (preconsumer scrap). The PET used can thus be virgin, scrap, recycled or reclaimed polyethylene terephthalate (PET). Advantageously, the PET is derived from PET molded articles (postconsumer scrap). Typically the waste PET comprises regrinds which are obtained by physically and mechanically grinding PET bottles into chips, powder, pellets or flakes. Furthermore in addition to polymers consisting only of terephthalic acid and ethylene glycol the PET as described herein may also comprise a modifying co-monomer such as cyclohexanedimethanol, isophthalic acid, and/or naphthalenedicarboxylic acid. The PET used in the process of the invention may be transparent or non-transparent, clear or colored or even have printing thereon.

By polyhydric alcohols (a1) is meant to designate compounds having at least two hydroxyl groups. They can be linear or branched, aliphatic and/or cycloaliphatic compounds. C3-C10 glycols are often preferred. Typically polyhydric alcohols (a1) are selected from one or more of: isosorbide, isomannide, isoiodide, 1,2-ethylene glycol, diethylene glycol, propylene glycol, dipropylene glycol, tripropylene glycol, 1,3-propanediol, polyethylene glycol, polypropylene glycol, 2-methyl-1,3-propanediol, 1,2-butandiol, 1,3-butanediol, 1,4-butanediol, 1,6-hexanediol, neopentyl glycol (2,2-dimethyl-1, 3-propandiol), 2-butyl-2-ethyl-1, 3-propanediol, 2,2,4-trimethyl-1,3-pentanediol, 3-methyl-1,5-pentanediol, ethoxylated neopentylglycol, propoxylated neopentylglycol, 1,4-cyclohexanedimethanol, bisphenol-A, ethoxylated bisphenol-A, hydrogenated bisphenol-A, an alkylene oxide adduct of hydrogenated bisphenolA, and trifunctional or higher functional polyhydric alcohols, such as glycerol, trimethylolpropane, ethoxylated trimethylolpropane, propoxylated trimethylolpropane, ethoxylated or propoxylated glycerol, pentaerythritol, ethoxylated pentaerythritol, propoxylated pentaerythritol, ditrimethylolpropane, di-pentaerythritol, ethoxylated dipentaerythritol and sorbitol. Preferred are trimethylolpropane, dipropylene glycol, tripropylene glycol, glycerol and/or propoxylated glycerol. Most preferred are trimethylolpropane, dipropylene glycol, tripropylene glycol and/or glycerol. Optionally, also at least one triglyceride or oil (a2) is used in step (a). The triglyceride can be a vegetable oil and/or can be an animal oil. In general the triglyceride (a2) used in the context of the invention is selected from one or more of: linseed oil, soybean oil, cotton seed oil, coconut oil, sunflower oil, rapeseed oil, safflower oil, hempseed oil, castor oil, lard oil and tallow oil. Vegetable oils in the context of the invention are preferred. Preferred are palm oil, rapeseed oil, soybean oil, sunflower oil, linseed oil, hemp oil, corn oil, castor oil and/or tall oil. Particularly preferred are palm oil, rapeseed oil, soybean oil, sunflower oil, linseed oil, hemp oil and/or corn oil. Most preferred are palm oil, rapeseed oil, soybean oil and/or sunflower oil. The advantage of incorporating one or more triglycerides in the structure of the (meth)acrylated compound (I) of the invention is that the triglyceride improves pigment wetting and is introduced via a transesterification reaction without the need to remove water.

The depolymerization reaction—step (a)—is preferably carried out at a temperature of between 160° C. and 260° C., preferably between 190° C. and 230° C. and most preferably between 215° C. and 225° C. Typically, the depolymerization reaction occurs over a period of between 1 and 12 hours, preferably between 2 and 4 hours e.g. 2-3 hours. Advantageously, the depolymerization reaction is carried out until the solid PET and polyhydric alcohol mixture is converted into a clear or homogeneous mixture or into a melt solution that contains no visible PET particles. The depolymerization reaction can be carried out at atmospheric, sub-atmospheric or supra-atmospheric pressures, but is preferably carried out at atmospheric pressure and under inert atmosphere.

The depolymerization product A (in casu PET polyol) that is obtained can range from a polymeric glass to a viscous liquid. Furthermore the color of the depolymerization product A depends on the quality of the PET material used. Typically, if low quality PET is used, for example postconsumer PET bottles with a large amount of insoluble impurities such as paper labels on the bottles or rub-off parts collected in the process of mechanical cutting of the bottles, then the depolymerization product is filtered after step (a).

The depolymerisation product A obtained in step (a) is then esterified in step (b). In step (b) of the process the depolymerization product obtained in step (a) is further reacted with (b1) at least one fatty acid and/or with (b2) at least one polybasic carboxylic acid different from (b1). Optionally, at least one polyhydric alcohol (b3) can be used as well. Optionally, at least one monomeric acid (b4) that is different from (b1) can be used as well. The monomeric acid in the context of the present invention advantageously is different from the (meth)acrylating compounds (c) described infra. Possibly the monomeric acid (b4) is a monomeric fatty acid.

The fatty acid (b1) that is used in the context of the present invention typically is a dimer fatty acid and/or trimer fatty acid, with dimer fatty acids being preferred. As used herein, the term "dimer fatty acid" is synonymous with "dimerized fatty acid" or "dimer acid". Dimer fatty acids are chemical intermediates made by dimerizing unsaturated fatty acids (e.g. oleic acid, linoleic acid, linolenic acid, ricinoleic acid) in the presence of a catalyst, such as a bentonite or montmorillonite clay. Commercially available dimer fatty acids are usually mixtures of products in which the dimerized product predominates. Some commercial dimer acids are made by dimerizing tall oil fatty acids. Dimer fatty acids frequently have 36 carbons and two carboxylic acid groups. They may be saturated or unsaturated. They may also be hydrogenated to remove unsaturation.

Fatty acids (b1) used in the context of the invention are typically selected from one or more of: dimerized oleic acid, trimerized oleic acid, dimerized linoleic acid, trimerized linolelic acid, dimerized linolenic acid, trimerized linolenic acid, or mixtures thereof. Suitable dimer fatty acids include Pripol™ dimer fatty acids (products of Croda) such as Pripol™ 1006, 1009, 1010, 1012, 1013, 1017, 1022, 1025, 1027, 1029, 1036, and 1098; Unidyme™ dimer acids (products of Arizona Chemical) such as Unidyme 10, 14, 18, 22, 35, M15, and M35; dimer acids available from Emery Oleochemicals, and FloraDyme™ dimer acids from Florachem Corporation. Preferred are dimerized oleic acid, dimerized linoleic acid and/or dimerized ricinoleic acid. Most preferred are dimerized oleic acid and/or dimerized linoleic acid. Most preferred is dimerized linoleic acid. The advantage of incorporating one or more fatty acids (typically dimer fatty acids) in the structure of the (meth)acrylated compound (I) of the invention is that it improves pigment wetting.

In the context of the present invention the term "polybasic carboxylic acid" is meant to extend to the corresponding anhydrides. Possibly a mixture of acids and anhydrides is used. Polybasic carboxylic acids (b2) are typically selected from one or more of: unsaturated polybasic acids, such as maleic acid, maleic anhydride, fumaric acid, and itaconic acid; aliphatic saturated polybasic acids, such as malonic acid, succinic acid, adipic acid, azelaic acid, and sebacic acid; aromatic saturated polybasic acids such as phthalic anhydride, isophthalic acid, terephthalic acid, trimellitic acid, 2,6-naphthalenedicarboxylic acid; and alicyclic polybasic acids, such as tetrahydrophthalic anhydride, hexahydro-4-methylphthalic anhydride (MHHPA), 1,2-hexahydrophthalic anhydride, 1,4-cyclohexanedicarboxylic acid, and nadic acid. A preferred acid derivative is a di-carboxy aromatic carboxylic acid anhydride. Preferred in the context of the invention are maleic acid, maleic anhydride, fumaric acid, succinic acid, adipic acid, isophthalic acid, phthalic acid, tetrahydrophthalic anhydride, 1,2-hexahydrophthalic anhydride and/or 1,4-cyclohexanedicarboxylic acid. Most preferred are adipic acid, phthalic acid and/or phthalic anhydride.

In step (c) the polyester polyol B is (meth)acrylated via reaction with at least one (meth)acrylating compound. This can be (meth)acrylic acid and/or a (meth)acrylic acid halide. Examples of suitable (meth)acrylic acid halides are (meth) acryloyl chloride. By (meth)acrylic is meant acrylic, methacrylic or a mixture of both. (Meth)acrylic acid and more in particular acrylic acid are preferred (meth)acrylating compounds (c).

Possibly the (meth)acrylating compound (c) is a mono- and/or poly(meth)acrylate adduct that is prepared from the condensation of a polyisocyanate molecule containing preferably two isocyanate groups with a mono- and/or poly (meth)acrylate molecule containing preferably one functionality capable to react with the isocyanates. This functionality is typically a hydroxyl group. By "mono(meth)acrylate" is meant that the compound contains one (meth)acryloyl group, by "poly(meth)acrylate" is meant that the compound contains two or more (meth)acryloyl groups. The reactants are typically reacted using a controlled stoechiometry implying an equivalent ratio of isocyanate: hydroxyl from 1:1 to 1:2, preferably from 1:1 to 1:1.5. The reaction is followed by recording the decrease of the isocyanate level I[NCO] up to the theoretical value corresponding to the completion of the reaction. The isocyanate content I[NCO] can be followed by the classical back titration method using dibutylamine.

Advantageously, the weight ratio of fatty acid (in casu dimer fatty acid) to the depolymerization product A is between 0 and 0.7. Usually this ratio is between 0 and 0.6 more in particular between 0 and 0.5. If a fatty acid (in casu dimer fatty acid) is used to produce the (meth)acrylated compound (I) of the invention then this ratio is typically between 0.1 and 0.7, more typically between 0.1 and 0.6 and most typically between 0.2 and 0.5. Advantageously, the weight ratio of polybasic carboxylic acid to the depolymerization product A is less than 0.3, preferably less than 0.25, most typically less than 0.2. Advantageously, the weight ratio of (meth)acrylating compounds (c) to the depolymerization product A is between 0.1 and 0.8, more in particular between 0.2 and 0.7, most typically between 0.3 and 0.6. The fatty acids (in casu dimer fatty acids) (b1), when used, are preferably added in an amount of less than 70 wt %, based upon the total weight of the depolymerization product A, and advantageously they are added in an amount of between 1 and 60 wt % and according to one embodiment between 10 and 60 wt %. The polybasic carboxylic acids (b2), when used, are preferably added in an amount of less than 40 wt % based upon the total weight of the depolymerization product A, and advantageously they are added in an amount of between 3 and 20 wt %.

Polyhydric alcohols (b3) may also be added to the reaction mixture in step (b) in order to form a polyester polyol B. The polyhydric alcohol(s) used in step (b) may be the same as the polyhydric alcohols used step (a). If used, then preferable tri-functional or higher-functional polyhydric alcohols are used such as glycerol, alkoxylated glycerol, trimethylol propane, alkoxylated trimethylolpropane, pentaerythritol and/or alkoxylated pentaerythritol. Preferred are glycerol and/or trimethylolpropane. When used at all, typically, the polyhydric alcohols (b3) are added in an amount of 40 wt % or less based on the weight of the depolymerization product A and advantageously they are then added in an amount of between 3 and 20 wt %. In a preferred embodiment of the invention, however, no polyhydric alcohols are used in step (b).

Furthermore, a mono-functional acid (c4), such as benzoic acid, may also be added to the reaction mixture during step (b).

The esterification reaction of step (b) is preferably carried out at a temperature of between 180° C. and 220° C. and preferably carried out in an inert atmosphere, such as nitrogen or argon. Typically the esterification reaction is carried out at pressure of between 5,000 to 150,000 Pa, preferably between 10,000 to 120,000 Pa and most preferably at atmospheric pressure. Typically, the esterification reaction is carried out until the acid value of the reaction mixture is reduced to between 2 to 50 mg KOH/g and preferably to between 2 to 30 mg KOH/g.

The polyester polyol produced in step (b) may be in the form of a clear viscous liquid or hard solid resin. Typically, the polyester polyol has a number average molecular weight (Mn) of between 500 to 5,000 Dalton (Da) and a weight average molecular weight (Mw) of between 1,000 to 10,000 Da. Additionally, the hydroxyl value of the polyester polyol is preferably at least 100, more preferably the hydroxyl value is between 150 and 800 and most preferably between 250 and 600 Da.

The polyester polyol B is then (met)acrylated in step (c). Typically, (meth)acrylic acid and usually acrylic acid is used. Alternatively, the (meth)acrylating compound used may be a (meth)acrylic acid halide. The (meth)acrylation of step (c) is preferably done in the presence of an acidic catalyst, such as methane sulfonic acid when (meth)acrylic acid is used. In case that a (meth)acrylic halide is used then a base catalyst is preferable used. Advantageously, (meth) acrylation is carried out in the presence of a polymerization inhibitor. Suitable inhibitors include phenols, such as 4-methoxyphenol or a copper or an aluminum based inhibitor. The (meth)acrylation of step (c) is carried out at a temperature of between 80° C. and 130° C., preferably between 90° C. and 110° C.

In the process of the invention, steps (b) and (c) can be subsequent steps. For instance, the condensation of the polyester polyol intermediate ("depolymerization product") A with at least one fatty acid (b1) and/or at least one polybasic carboxylic acid (b2) and optionally at least one polyhydric alcohol (b3), can be done after the depolymerization step without solvent. Condensation with at least one (meth)acrylating compound (c), is then done afterwards, using an azeotropic solvent to remove water. Alternatively, the condensation of the polyester polyol intermediate A with a mixture of at least one fatty acid (b1) and/or at least one polybasic carboxylic acid (b2) and at least one (meth) acrylating compound (c) (typically acrylic acid) and, optionally, at least one polyhydric alcohol (b3) can be done using a azeotrope solvent to remove water. Steps (b) and (c) hence can also be carried out at the same time. In the above, the fatty acid advantageously is a dimer fatty acid, possibly a trimer fatty acid.

(Meth)acrylated compounds (I) of the invention advantageously incorporate the residues of at least one triglyceride (a2) and/or of at least one fatty acid (b1) (which typically is a dimer fatty acid). In one embodiment of the invention the (meth)acrylated compound (I) obtained contains the residues of at last one triglyceride and advantageously no residue of at least one fatty acid. In another embodiment of the invention the (meth)acrylated compound (I) obtained contains the residues of at last one fatty acid, and advantageously no residue of at least one tiglyceride. In yet another embodiment of the invention the (meth)acrylated compound (I) obtained contains the residues of at last one fatty acid and at least one triglyceride. As before, the fatty acid (b1) advantageously is a dimer fatty acid, possibly a trimer fatty acid.

Another aspect of the invention relates to a (meth)acrylated compound (I) obtained by or obtainable by a process according to the invention. (Meth)acrylated compounds (I) of the invention typically have a number average molecular weight (Mn) of between 500 and 5,000 Dalton (Da). The Mn usually is at least 700 Da, more typically at least 3,000 Da. The Mn usually is at most 2,000 Da, more typically at most 1,700 Da. The (meth)acrylated compound (I) usually has a weight average molecular weight (Mw) of between 800 and 10,000 Da. Typically the (meth)acrylic acid ester group content is between 1 to and 6 mmol/g. Preferably the (meth)acrylated compound (I) of the invention has an acid value of between 2 and 50 mg KOH/g.

Preferred compounds (I) of the invention are those that have a polyalkylene terephthalate content of at least 15 wt %, relative to the total weight of the (meth)acrylated compound (I). In general this content is at least 20 wt %, more typically this content is at least 25 wt %. Most typically the polyalkylene terephthalate is PET. Hence, provided in the invention is a (meth)acrylated compound (I) with a PET content of at least 15 wt %, relative to the total weight of the (meth)acrylated compound (I). In general the PET content is at least 20 wt %, more typically this content is at least 25 wt %.

The (meth)acrylated compound (I) of the invention typically has a viscosity at 25° C. that is below 500 Pas, more preferably below 300 Pas and most preferably below 200 Pa.

Preferred compounds (I) of the invention are polyester (meth)acrylates and/or polyurethane (meth)acrylates. Particularly preferred are polyester (meth)acrylates and/or urethane (meth)acrylates The latter are for instance formed if the (meth)acrylating compound (c) is an adduct between a polyisocyanate and a hydroxyalkyl (meth)acrylate.

(Meth)acrylated compound (I) of the invention have the advantage that they can be easily incorporated into (or used in) e.g. coating compositions, adhesives, varnishes, lacquers or inks that then advantageously exhibit an improved pigment wetting and/or an improved ink-water balance. Another aspect of the invention hence relates to an energy curable composition (II), in particular to a radiation curable composition that is prepared from a (meth)acrylated compound (I) according to the invention.

The energy curable composition (II) can be a coating composition, a varnish, a lacquer, ink or adhesive.

Coating compositions or inks according to the invention typically comprise from 1 to 80 wt %, preferably from 5 to 70 wt %, more preferably from 10 to 60 wt % and advantageously from 15 to 50 wt % of one or more (meth) acrylated compounds (I) of the invention.

Energy curable coating compositions or inks of the invention may additionally contain other (meth)acrylated oligomers (d), typically with an acrylate functionality >2, such as epoxy (meth) acrylates, polyester (meth)acrylates, urethane (meth)acrylates, polyurethane (meth)acrylates, (meth)acrylated polyacrylates, polyether (meth)acrylates, (meth)acrylated oils based on linseed oil, soybean or castor oil and mixtures thereof. By "other" is meant a compound different from the (meth) acrylated compound (I) of the invention.

The weight average molecular weight (Mw) of the other (meth) acrylated oligomers (d) is usually between 400 to 3,000 Da. The other (meth)acrylated oligomers are typically incorporated in the coating compositions or inks to impart rheology, pigment wetting, transfer, gloss, chemical resistance and other film properties.

Furthermore, the energy curable coating compositions or inks may additionally contain (met)acrylic monomers (e) that are typically esters of (met)acrylic acid having a functionality >2. Acrylic monomers are preferred. The weight average molecular weight (Mw) of the (meth)acrylic monomers (e) is usually between 200 and 800 Da. Typically the energy curable coating compositions and inks of the invention contain between 15 and 45 wt % of acrylic monomers, preferably between 20 and 40 wt % and most preferably between 25 and 35 wt %. These (meth) acrylic monomers are incorporated into the coating compositions or inks to impart curing speed, solvent resistance, hardness and allow viscosity adjustment.

The (meth)acrylated oligomers (d) and (meth)acrylic monomers (e) may be selected from 1,2-ethylene glycol diacrylate, 1,4-butandiol diacrylate, 1,6-hexandiol diacrylate, dipropylene glycol diacrylate, isosorbide diacrylate, neopentylglycol diacrylate, ethoxylated neopentylglycol diacrylates, propoxylated neopentylglycol diacrylates, tripropylene glycol diacrylate, bisphenol-A diacrylate, ethoxylated bisphenol-A-diacrylates, bisphenol-A-diglycidylether diacrylate, ethoxylated bisphenol-A-diacrylates, poly(ethylene)glycol diacrylates, trimethylolpropane triacrylate, trimethylolpropane trimethacrylate, ethoxylated trimethylolpropane triacrylates, propoxylated trimethylolpropane triacrylates, propoxylated glycerol triacrylates, pentaerythritol triacrylate, ethoxylated pentaerythritol triacrylates, propoxylated pentaerythritol tetraacrylates, ethoxylated pentaerythritol tetraacrylates, ditrimethylolpropane tetraacrylate, dipentaerythritol pentaacrylate, dipentaerythritol hexaacrylate ethoxylated dipentaerythritol hexaacrylates or mixtures thereof, and are preferably ethoxylated trimethylolpropane triacrylates, ethoxylated pentaerythritol triacrylates and propoxylated pentaerythritol tetraacrylates.

In particular, when the coating composition or ink is formulated for food packaging, multifunctional acrylates such as ethoxylated pentaerythritol tetraacrylates, ditrimethylolpropane tetraacrylate, dipentaerythritol pentaacrylate, dipentaerythritol hexaacrylate, ethoxylated dipentaerythritol hexaacrylates or mixtures thereof are preferred.

The energy curable coating compositions or inks of the invention may also contain one or more colorants in the form of a dye or pigment dispersed therein. Suitable pigments include conventional organic or inorganic pigments.

The energy curable coating compositions or inks of the invention are advantageously UV curable and typically contain photoinitiators, such as for example benzophenones, benzilketales, dialkoxy acetophenones, hydroxyalkyl-acetophenones, aminoalkylphenones, acylphosphinoxides and thioxanthones, for example benzophenone, methylbenzophenone, 4-phenylbenzophenone, 4,4'-bis(dimethylamino)-benzophenone, 4,4'-bis(diethylamino)-benzophenone, 2,2-dimethoxy-2-phenylacetophenone, dimethoxyacetophenone, diethoxy-acetophenone, 2-hydroxy-2-methyl-1-phenylpropan-1-one, 2-benzyl -2-dimethylamino-1-(4-mo holinophenyl)-butan-l-one, 2-methyl-l-[4 (methoxythio)-phenyl]-2-mo holinopropan-2-one, diphenylacylphenyl phosphinoxide, diphenyl(2,4,6-trimethylbenzoyl) phosphinoxide, 2,4,6-trimethylbenzoylethoxyphenyl phosphinoxide, 2-isopropylthioxanthone, 4-isopropylthioxanthone, 2,4-dimethylthioxanthone or mixtures thereof.

Alternatively, the energy curable coating compositions or inks of the invention may be cured thermally with e.g. peroxides.

Furthermore the energy curable coating compositions or inks of the invention may further contain the usual additives to modify flow, surface tension, gloss, pigment wetting and abrasion resistance of the cured coating or printed ink. Such additives include surface active agents, waxes, shelf-life stabilizers, and combinations thereof. These additives may function as leveling agents, shelf-life stabilizers, wetting agents, slip agents, flow agents, dispersants and de-aerators. Preferred additives include fluorocarbon surfactants, silicones and organic polymer surfactants. Furthermore the energy curable coating compositions or inks may further contain the usual extenders such as clay, talc, calcium carbonate, magnesium carbonate or silica to adjust water uptake, misting and color strength.

A good flow is maintained when adding fillers (e.g. fumed silica), good pigment wetting may also be obtained with materials according to the invention.

Typically, the energy curable coating compositions or inks for offset have a viscosity of between 5 and 150 Pas, preferably between 20 and 60 Pas at a shear rate of D=50 1/s, Flexographic inks typically have a viscosity at 25° C. that is between 0.5 Pa.s and 5 Pa.s and preferably between 0.5 and 1.5 Pa.s. Advantageously, the energy curable coating compositions or inks of the invention are energy curable lithographic inks.

The present invention also provides articles that are coated or printed, either entirely or in part, with coating compositions or inks according to the invention. The coating compositions or inks are typically applied to the articles using inkjet, flexo, gravure, screen, and litho printing and are subsequently cured.

The articles may be composed of any typical substrate such as paper, plastics, metals and composites. The substrate may be paper print stock typically used for publications or may be a packaging material in the form of a cardboard sheet or corrugated board. Furthermore, the substrate may be a polyolefin, such as a polyethylene or a polypropylene, a polyester such as polyethylene terephthalate, or a metalized foil such as an laminated aluminum foil or a metalized polyester.

The coating compositions or inks of the invention may be cured using an electron beam (EB) but are preferably cured using ultraviolet light (UV). The compositions may be cured by an actinic light source, such as for example UV-light, provided by a high-voltage mercury bulb, a medium-voltage mercury bulb, a xenon bulb, a carbon arc lamp, a metal halide bulb, a UV-LED lamp, a UV laser, such as a semiconductor laser or an eximer laser or sunlight. The wavelength of the applied radiation is preferably within a range of between 200 and 500 nm, more preferably between 250 and 350 nm.

EXAMPLES

The following examples illustrate specific aspects of the present invention and are not intended to limit the scope thereof in any respect and should not be so construed.

Measuring Methods

Molecular weights (Mn or Mw) typically are determined via gel permeation chromatography (GPC), typically using polystyrene standards. Most typically the Mn and Mw are measured by GPC (in a tetrahydrofuran (THF) solution, injected on a 3× PLgel 5 μm Mixed-D LS 300×7.5 mm column MW—range 162 to 377400 Daltons & calibrated with polystyrene standards (200-400.000 Daltons), at 40° C.

Acid Value and Hydroxyl Value

Acid value: total acid number (IAc in mg KOH/g) was measured using potentiometric titration. The "total acid number" equals the milligrams of potassium hydroxide (KOH) required to neutralize the acid(s) present in I g of sample after hydrolysis of present anhydrides. The anhydrides present in the sample are hydrolysed to the corresponding acids during a hydrolysis step and titrated with a standardized solution of KOH. Different titrant solutions i.e. KOH 0.1 N and/or KOH 0.5 N can be used when analyzing samples with low respectively high total acid number. Potentiometric titration allows end-point identification automatically by means of a titroprocessor and a pH electrode, the manual titration uses a color indicator (phenolphthalein) or visual end-point identification. The amount of KOH is used to calculate the total acid number.

Hydroxyl values (IOH in mg KOH/g) were measured using the following method. This "OH Number" method covers the automated quantification procedure for hydroxyl groups in polyester resins by means of potentiometric titration. The hydroxyl number is defined as the number of milligrams of potassium hydroxide required to neutralize the hydrolysis product of the fully acetylated derivative prepared out of one gram of polyester resin. Step I Acetylation step: All hydroxyl functions on the polyester resin are acetylated at room temperature by acetic anhydride in the presence of perchloric acid as catalyst. Dichloromethane (=methylene chloride CH2C12) functions as solvent. Step 2 Hydrolysis step: The excess of acetic anhydride is hydrolysed by means of water, N-methyl-2-pyrrolidone (NMP) functions as co solvent to dissolve water in methylene chloride and N-methylimidazole (NMI) functions as hydrolysis catalyst. Step 3 Titration step: The formed acid functions are titrated with KOH 0.5 N solution.

Pigment Wetting Can be Evaluated by Different Methods

Rheology: Pigment wetting is a major factor of influence on the rheology. Inks with bad wetting of the pigment are showing a marked shear thinning effect, whereby the viscosity is high at low shear rate and drops as the shear rate is increased. This results in a high shortness index (SI=ratio of low shear viscosity to high shear viscosity. For liquid inks a Newtonian rheology is required. Ideally, this means that the viscosity is independent of the shear rate. (SI=1). Paste inks are more pseudoplastic, showing a shear depending viscosity. (SI>1). Too high SI (too high low shear viscosity) may result in bad flow in the ink duct.

Optical density: Pigment wetting can also be evaluated by measuring the color density of the printed ink at constant film thickness. In this case the ink is printed using a lab applicator and the color density is measured with a densitometer, which spectrophotometrically compares the reflected light to the incident light.

For the present invention the pigment wetting is rated on a scale from 5=excellent to 0=bad pigment wetting.

Rheology (yield value, viscosity, shortness index) is measured using a cone and plate type rheometer MCR100 (Paar-Physica). The measurement geometry for measuring the UV offset inks was of a diameter of 25 mm and an angle of 1° for the cone. The measurement was a flow curve in controlled shear rate ranging from D=0.1 s-1 to D=100 s-1 at 25° C. The measurement geometry for measuring the UV screen inks of Example 2 was of a diameter of 50 mm and an angle of 1° for the cone. The measurement was a flow curve in controlled shear rate ranging from D=0.1 s-1 to D=500 s-1 at 25° C.

The ink water balance of the compositions of the present invention was evaluated on Lithotronic.

Basically, the Lithotronic measures the torque needed for a certain speed (rpm). The torque gives a measure for viscosity. With the Lithotronic, the change in viscosity of an ink is measured when water is emulsified in it.

The measurement consists of two phases: preconditioning and measurement.

During preconditioning, the sample is sheared at constant speed and heated at the same time to a certain preprogrammed temperature. At the end of the preconditioning phase, the sample has reached a stable viscosity. At that moment, controlled metering of fount solution is started. Changes of applied torque (hence viscosity) versus time and emulsion capacity are recorded. When maximum emulsion capacity is reached, a drop in torque is usually experienced because of the free water in the beaker.

At first contact with water, change of torque (delta T) should be small. Further, when water is emulsified in the ink, viscosity should only undergo a minor increase. This ensures a good ink transfer on the press. If the emulsion is too fine and too stable (too high increase of viscosity), it will lead to a loss of density and possible ink build up. If the emulsion is too coarse (viscosity decrease), it can lead to unstable press behavior making regular press control necessary.

For the present invention the ink water balance is rated by the type of emulsion (F=good ink water balance characterized by a limited viscosity increase, resulting from a fine emulsion; C=bad ink water balance characterized by a high viscosity decrease, resulting from a coarse emulsion).

Synthesis

A double jacket (oil heated) reactor equipped with an overhead mixer, condenser, thermocouple, and nitrogen inlet is charged with catalyst, recycled polyethylene terephthalate (PET) pellets, glycol (TMP, DPG, TPG or glycerol) and triglyceride in the molar proportions shown in Tables 1 & 2. The mixture is heated at 230° C. under nitrogen flow without stirring until no particles of recycled PET remains (about 2 h). When PET particles have disappeared, the mixture is further heated and stirred for 2 to 4 hours. The mixture is cooled to about 80° C., a Dean-Stark trap is introduced between the reactor and condenser, toluene, methanesulfonic acid (70wt % in water), hydroquinone, methylhydroquinone, adipic acid, phthalic acid, dimer fatty acid and acrylic acid are added (see weights in g in Table 1). The mixture is stirred and heated at reflux until roughly the theoretical water amount is removed. When the reaction is complete, the polyester acrylate is allowed to cool to 90° C. and is decanted from the reactor and filtered through filter bags from 5 and 1 micron. Toluene is then evaporated.

Examples in Inks

Polyester acrylates thus obtained were then formulated into the following litho and flexo inks with compositions as given in Table 3. Results obtained with these are summarized in Tables 4 and 5.

Ink formulations according to the invention (FL EX 2, FL EX 4, FL EX 5, FL EX 7, FL EX 8 and FL EX 9) have better ink-water balance properties→lower Delta Torque and lower Delta tack than the ink according to FL COMP-2R (based on a polyester acrylate prepared without a triglyceride and/or a dimer fatty acid) [Table 4]. Ink formulations according to the invention (FL EX3 and FL EX6) have better low and higher gloss on PP (polypropylene) than the ink according to FL COMP-1R (based on a polyester acrylate prepared without a triglyceride and/or a dimer fatty acid) [Table 5].

TABLE 1

Step (a)

| POLYESTER POLYOL INTERMEDIATE (PP) | PP 1 | PP 2 | PP 3 | PP 4 | PP 5 | PP 6 | PP 7 |
|---|---|---|---|---|---|---|---|
| PET (mol) | 1 | 1 | 1 | 1 | 1 | 1 | 1 |
| TMP (mol) | 0.225 | — | — | — | — | — | 0.4 |
| DPG (mol) | 1.275 | 0.75 | 1 | — | — | — | — |
| TPG (mol) | — | — | — | 0.3 | 0.3 | — | — |
| Glycerol (mol) | — | 0.75 | 0.5 | 0.6 | 0.6 | 0.3 | — |
| Propoxylated glycerol | — | — | — | — | — | 0.9 | 0.7 |
| Triglyceride nature | — | — | — | Palm oil | Sun flower oil | — | — |
| Triglyceride (mol) | — | — | — | 0.1 | 0.1 | — | — |
| Mol ratio Glycol /PET | 1.5 | 1.5 | 1.5 | 0.9 | 0.9 | 1.2 | 1.1 |
| Wt ratio Glycol/PET | 1.05 | 0.88 | 0.94 | 0.59 | 0.73 | 1.53 | 1.35 |
| Mol ratio triglyceride/PET in prepolymer | 0 | 0 | 0 | 0.1 | 0.1 | 0 | 0 |
| Wt ratio triglyceride/PET | 0 | 0 | 0 | 0.46 | 0.49 | 0 | 0 |
| IOH mg KOH/g | 432 | 579 | 526 | 278 | 266 | 414 | 408 |
| PET Wt % | 49 | 53 | 52 | 49 | 49 | 40 | 42 |
| Triglyceride wt % | 0 | 0 | 0 | 22 | 22 | 0 | 0 |
| Catalyst (ppm) | 3000 | 3000 | 3000 | 3000 | 3000 | 3000 | 3000 |
| Mn | 640 | 579 | 642 | 850 | 870 | 790 | 920 |
| Visc Mpas at 25° C. or at 60° C. | 5740 (25° C.) | 748 (60° C.) | 9800 (25°) | 1343 (60° C.) | 995 (60° C.) | 64520 (25°) | 2566 (60°) |

TABLE 2

Steps (b) and (C)

| PEA RESIN | COMP-1R | COMP-2R | EX 2 | EX 3 | EX 4 | EX 5 | EX 6 | EX 7 | EX 8 | EX 9 |
|---|---|---|---|---|---|---|---|---|---|---|
| Polyesterpolyol intermediate (g) | PP1 (2143) | PP1 (410) | PP2 (312) | PP3 (346) | PP4 (505) | PP5 (580) | PP1 (312) | PP2 (312) | PP6 (300) | PP7 (400) |
| Adipic acid (g) | 374 | 18.4 | 37 | 37 | 18 | 34 | 29 | — | — | 42 |
| Phthalic anhydride (g) | — | 56.0 | — | — | — | — | — | 37 | — | — |
| Trimellitic anhydride (g) | — | — | — | — | — | — | — | — | 16 | — |
| Dimer fatty acid (g) | — | — | 148 | 146 | — | — | 115 | 145 | 88 | 27 |
| Acrylic acid (g) | 892 | 159 | 173 | 175 | 162 | 165 | 138 | 174 | 96 | 128 |
| MSA (aq 70%) | 52.4 | 13.0 | 10.3 | 10.8 | 10.6 | 12.0 | 9.1 | 16 | 15 | 17 |
| Toluene (g) | 1835 | 319 | 359 | 379 | 369 | 419 | 320 | 281 | 269 | 307 |
| HQ (g) | 0.6 | 0.12 | 0.15 | 0.13 | 0.13 | 0.15 | 0.11 | 0 | 0 | 0 |
| MeHQ (g) | 4.6 | 0.89 | 0.91 | 0.75 | 0.96 | 1.09 | 0.65 | 0.61 | 0.47 | 0.55 |
| Wt ratio adipic acid (+phthalic anh)/polyester polyol | 0.17 | 0.18 | 0.12 | 0.11 | 0.036 | 0.06 | 0.09 | 0.12 | 0.053 | 0.10 |
| Wt ratio dimer fatty acid/polyester polyol | 0 | 0 | 0.46 | 0.42 | 0 | 0 | 0.37 | 0.46 | 0.29 | 0.066 |
| Wt ratio acrylic acid/polyester polyol | 0.42 | 0.39 | 0.56 | 0.51 | 0.32 | 0.28 | 0.44 | 0.56 | 0.32 | 0.32 |
| PET Wt % | 34 | 32 | 26 | 34 | 39 | 39 | 33 | 25 | 21 | 31 |
| Triglyceride wt % | 0 | 0 | 0 | 0 | 17 | 17 | 0 | 0 | 0 | 0 |
| Mn | 1890 | 890 | 1610 | 1420 | 1320 | 1300 | 1210 | 1350 | 1840 | 1750 |
| Visc Mpas 25° C. | 5726 | 38400 | 66039 | 20668 | 49387 | 45485 | 8266 | 64058 | 109720 | — |

TABLE 3

Composition and viscosity of the polyester (meth)acrylates prepared

| RESIN | COMP-1R | EX 2 | EX 3 | EX 4 | EX 5 |
|---|---|---|---|---|---|
| PP | PP1 | PP2 | PP3 | PP4 | PP5 |
| Triglyceride | — | — | — | Palm oil | Sun flower oil |
| Dimer fatty acid | — | Dimer acid | Dimer acid | — | — |
| Viscosity (mPas @ 25° C.) | 5726 | 66039 | 20668 | 49387 | 45485 |

TABLE 4

Cyan Offset Litho Inks (amounts in g)

| FORMULATION | FL COMP-2R | FL EX 2 | FL EX 4 | FL EX5 | FL EX7 | FL EX8 | FL EX9 |
|---|---|---|---|---|---|---|---|
| Resin COMP-2R | 67 | | | | | | |
| Resin Ex 2 | | 65.5 | | | | | |
| Resin Ex 4 | | | 68 | | | | |
| Resin Ex 5 | | | | 67 | | | |
| Resin Ex 7 | | | | | 64 | | |
| Resin Ex 8 | | | | | | 60 | |
| Resin Ex 9 | | | | | | | 61 |
| OTA (Glycerol propoxylated triacrylate) | 0 | 3 | 0 | 0 | 4 | 8 | 8 |
| Stabilizer | 0.1 | 0.1 | 0.1 | 0.1 | 0.1 | 0.1 | 0.1 |
| Pigment Cyan 15:3 | 20 | 20 | 20 | 20 | 20 | 20 | 20 |
| Photoinitiator blend | 8 | 8 | 8 | 8 | 8 | 8 | 8 |
| OTA | 5 | 3.5 | 4 | 5 | 4 | 4 | 3 |
| Total | 100.1 | 100.1 | 100.1 | 100.1 | 100.1 | 100.1 | 100.1 |
| RESULTS | | | | | | | |
| Viscosity 2.5 1/s (Pa · s) | 79.1 | 71.4 | 91.5 | 94.4 | 79.5 | 68.9 | 85 |
| Viscosity 100 1/s (Pa · s) | 39.5 | 35.2 | 34.1 | 34.8 | 38.2 | 35.6 | 42.2 |
| Cure speed 140 W/cm (m/min) | 25 | 25 | 30 | 20 | 20 | 20 | 15 |
| INK WATER BALANCE-LITHOTRONIC | | | | | | | |
| Delta Torque (%) | 35 | 20 | 23 | 25 | 24 | 25 | 22 |
| Emulsion Capacity % | 50 | 64 | 60 | 56 | 60 | 58 | 55 |
| INK WATER BALANCE-HYDROSCOPE | | | | | | | |
| Emulsification Point (%) | 43 | 20 | 36 | 39 | 18 | 38 | 35 |
| Tack after 1 min stabilty | 440 | 400 | 380 | 380 | 415 | 375 | 420 |
| Tack decay in % | 52 | 42 | 52 | 52 | 40 | 52 | 33 |
| Tack end test | 480 | 400 | 390 | 390 | 415 | 380 | 420 |
| Delta tack (%) end test | +9 | 0 | 3 | 3 | 0 | 1 | 0 |

Ink formulations according to the invention (FL EX 2, FL EX 4, FL EX 5, FL EX 7, FL EX 8 and FL EX 9) have better ink-water balance properties → lower Delta Torque and Detla tack % than the ink according to FL COMP-2R (based on a polyester acrylate prepared without a triglyceride and/or a dimer fatty acid).

TABLE 5

Magenta Flexo Inks (amounts in g)

| FORMULATION | FL COMP-1R | FL EX6 | FL EX3 |
|---|---|---|---|
| Resin COMP-1R | 27.6 | — | — |
| Resin EX 6 | — | 27.6 | — |
| Resin EX 3 | — | — | 24.6 |
| EBECRYL 160 | — | — | 3.0 |
| Stabilizer | 0.1 | 0.1 | 0.1 |
| Dispersing agent | 2.4 | 2.4 | 2.4 |
| Pigment Red 57:1 | 16.0 | 16.0 | 16.0 |
| Grinding | | | |
| EBECRYL 160 | 46.0 | 46.0 | 46.0 |
| EDB | 5.0 | 5.0 | 5.0 |
| PBZ | 3.0 | 3.0 | 3.0 |
| Total | 100.1 | 100.1 | 100.1 |
| RESULTS | | | |
| Viscosity 0.1 1/s (mPa · s) | 1260 | 1020 | 1050 |
| Viscosity 2500 1/s (mPa · s) | 605 | 650 | 625 |
| Shortness Index 0.1-2500 | 2.1 | 1.6 | 1.7 |
| REACTIVITY | | | |
| Cure speed 140 W/cm- 1.5 g/m² - Air (m/min) | 25 | 25 | 30 |
| Blocking Test 140 W/cm - 100 m/min | 3x | 3x | 3x |
| Optical Density (1.5 g/m²) | 1.4 | 1.5 | 1.5 |
| Gloss on PP (1.5 g/m²) | 90 | 97 | 98 |
| Flow after 30 sec (cm) | 24 | 30 | 30 |
| Time for 30 cm flow (sec) | 45 | 30 | 30 |

Ink formulations according to the invention (FL EX3 and FL EX6) have better low and higher gloss on PP (polypropylene) than the ink according to FL COMP-1R (based on a polyester acrylate prepared without a triglyceride and/or a dimer fatty acid).

The invention claimed is:

1. A process for preparing a (meth)acrylated compound (I) comprising the steps of:
    (a) reacting a thermoplastic polyester with (a1) at least one polyhydric alcohol and, optionally, with (a2) at least one triglyceride, wherein, when present, the molar ratio of triglyceride to thermoplastic polyester is between 0 and 0.3, and the molar ratio of polyhydric alcohol to thermoplastic polyester is at most 1.9 to obtain a depolymerization product A with a hydroxyl number within the range of from 200 to 800 mg KOH/g;
    (b) reacting the depolymerization product A with (b1) at least one fatty acid and/or (b2) at least one polybasic carboxylic acid and, optionally, with (b3) at least one polyhydric alcohol to provide a polyester polyol B;
    (c) reacting the polyester polyol B with (c1) at least one (meth)acrylating compound to provide a (meth)acrylated compound (I),
    wherein the weight ratio of fatty acid (b1), when present, to the depolymerization product A is between 0 and 0.6,
    wherein the weight ratio of polybasic carboxylic acid (b2), when present, to the depolymerization product A is less than 0.3,
    wherein the weight ratio of (meth)acrylating agent to the depolymerization product A is between 0.1 and 0.8, and
    wherein the (meth)acrylated compound (I) has a number average molecular weight (Mn) between 500 and 5000 Da.

2. The process of claim 1, wherein the molar ratio of polyhydric alcohol (a1) to thermoplastic polyester is lower than 1.8.

3. The process of claim 1, wherein the molar ratio of triglyceride (a2) to thermoplastic polyester is between 0.01 and 0.25.

4. The process of claim 1, wherein the thermoplastic polyester in step (a) is selected from one or more of the group consisting of: polyethylene naphthalate (PEN); polyethylene terephthalate (PET); polypropylene terephthalate (PPT); polybutylene terephthalate (PBT); polytrimethylene terephthalate; glycol-modified polyethylene terephthalate; copolymers of terephthalic acid and 1,4-cyclohexanedimethanol; isophthalic acid-modified copolymers of terephthalic acid and 1,4-cyclohexanedimethanol; polyhydroxy alkanoates; copolymers of diols with 2,5-furandicarboxylic acid or dialkyl 2,5-furandicarboxylates; copolymers of 2,2,4,4-tetramethyl-1,3-cyclobutanediol with isophthalic acid, terephthalic acid or orthophthalic derivatives; and dihydroferulic acid polymers.

5. The process of claim 4, wherein the thermoplastic polyester is derived from waste material generated in the production of PET or in the production of PET molded articles.

6. The process of claim 1, wherein the depolymerization product A that is formed in step (a) has a hydroxyl number of from 200 to 700 mg KOH/g.

7. The process of claim 1, wherein the (b1) at least one fatty acid is/are dimer fatty acids (b1), the dimer fatty acids (b1) being added in step (b) in an amount of less than 70 wt %, based upon the total weight of the depolymerization product A.

8. The process of claim 7, the dimer fatty acids (b1) being added in step (b) in an amount from 1 to 60 wt %.

9. The process of claim 1, wherein polybasic carboxylic acids (b2) are added in step (b) in an amount of less than 40 wt %, based upon the total weight of the depolymerization product A.

10. The process of claim 1, wherein at least one polyhydric alcohol (b3) is added to the reaction mixture in step (b).

11. The process of claim 1, wherein at least one monofunctional acid (b4) is added to the reaction mixture in step (b).

12. The process of claim 1, wherein the weight ratio of (meth)acrylating compounds to the depolymerization product A is between 0.1 and 0.8.

13. The process of claim 1, wherein the hydroxyl number is measured by titration of acetic acid after acetylation of hydroxyl groups and hydrolysis of acetic anhydride excess.

14. A (meth)acrylated compound (I) prepared by a process of claim 1, wherein the (meth)acrylated compound (I) has a PET content of at least 15 wt %.

15. A radiation curable composition that is an ink, a varnish, a lacquer, a coating composition or an adhesive prepared from a (meth)acrylated compound (I) according to claim 14.

16. An article, coated or printed, entirely or in part, with a radiation curable composition according to claim 15.

17. A (meth)acrylated compound (I) prepared by a process of claim 1, wherein the (meth)acrylated compound (I) has a PET content of at least 25 wt %.

* * * * *